United States Patent [19]

Garcia

[11] Patent Number: 5,349,966
[45] Date of Patent: Sep. 27, 1994

[54] HANDS RESTRAINT FOR HANDCUFFED WRISTS

[76] Inventor: Joseph L. Garcia, 2408 Pleasure House Rd., Virginia Beach, Va. 23455

[21] Appl. No.: 989,144

[22] Filed: Dec. 11, 1992

[51] Int. Cl.⁵ ............................................... A61F 5/37
[52] U.S. Cl. ...................................... 128/879; 2/158; 2/16
[58] Field of Search .................... 2/16, 20, 158, 159, 2/160, 162, 64, 66; 128/878, 879; 70/16, 18

[56] References Cited

U.S. PATENT DOCUMENTS

| | | | |
|---|---|---|---|
| 973,330 | 10/1910 | Wood | 2/158 X |
| 1,529,546 | 3/1925 | McKenzie | 2/158 X |
| 3,182,657 | 5/1965 | Zurbuchen | 2/20 X |
| 3,741,207 | 6/1973 | Fuson | 2/16 X |
| 5,031,641 | 7/1991 | Upton | 128/879 |
| 5,050,596 | 9/1991 | Walesek et al. | 2/158 X |

FOREIGN PATENT DOCUMENTS 2903535  8/1980  Fed. Rep. of Germany ......... 2/159

*Primary Examiner*—Clifford D. Crowder
*Assistant Examiner*—Gloria Hale
*Attorney, Agent, or Firm*—John K. Donaghy

[57] ABSTRACT

A restraint for hands having hand cuffed wrists comprises: an inner pouch for use to separate the hands; an outer pouch for use over the inner pouch; and the provision on the outer pouch for securing the inner pouch and the outer pouch to handcuffed wrists.

3 Claims, 2 Drawing Sheets

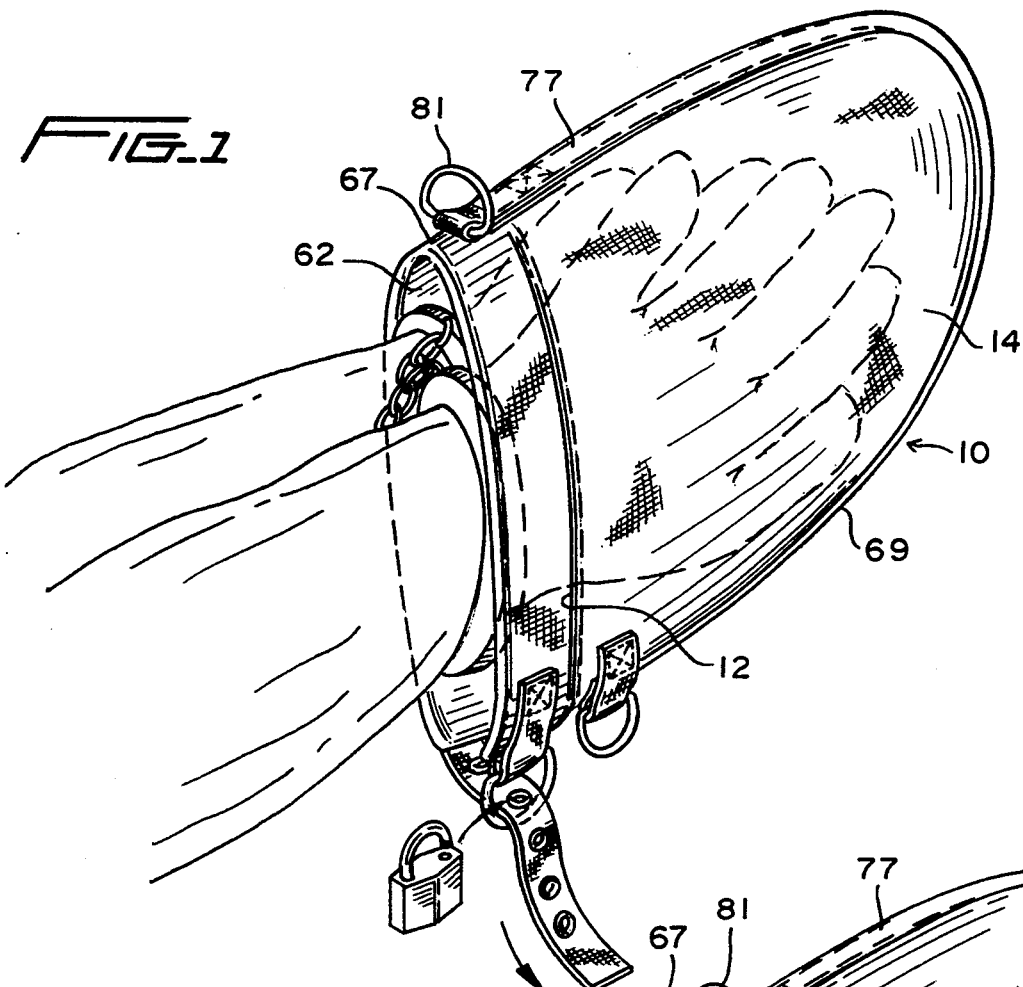
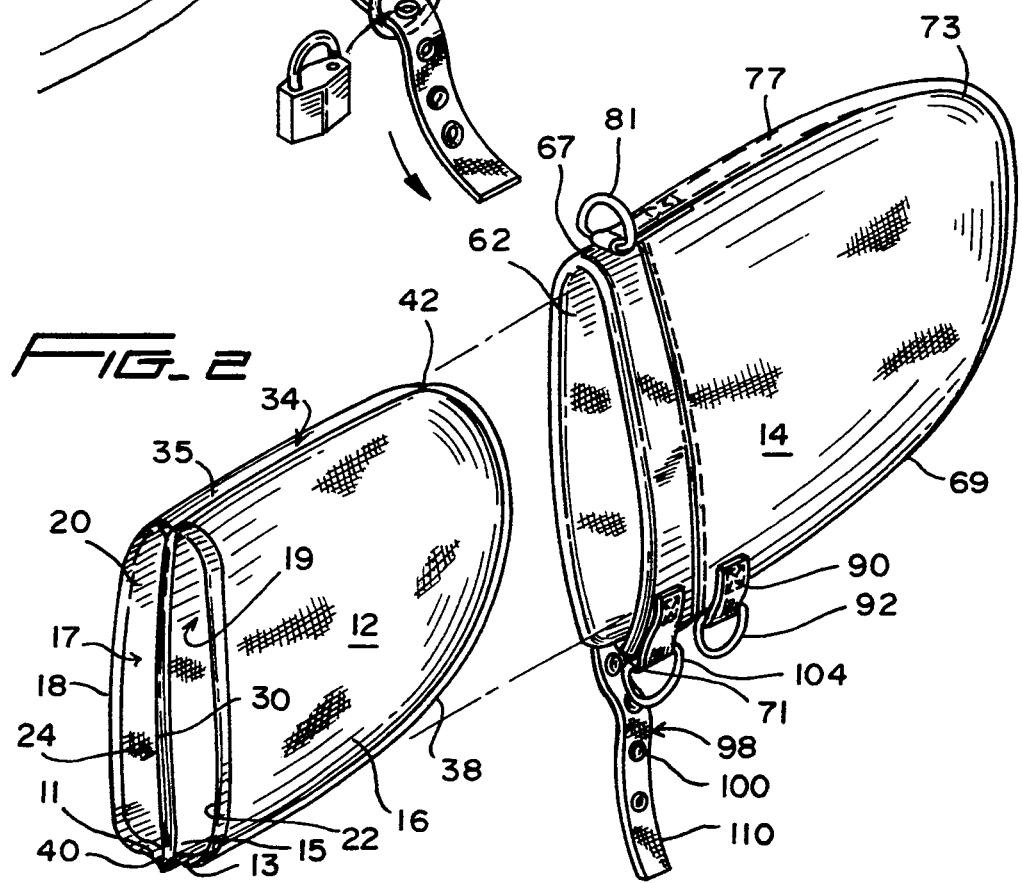

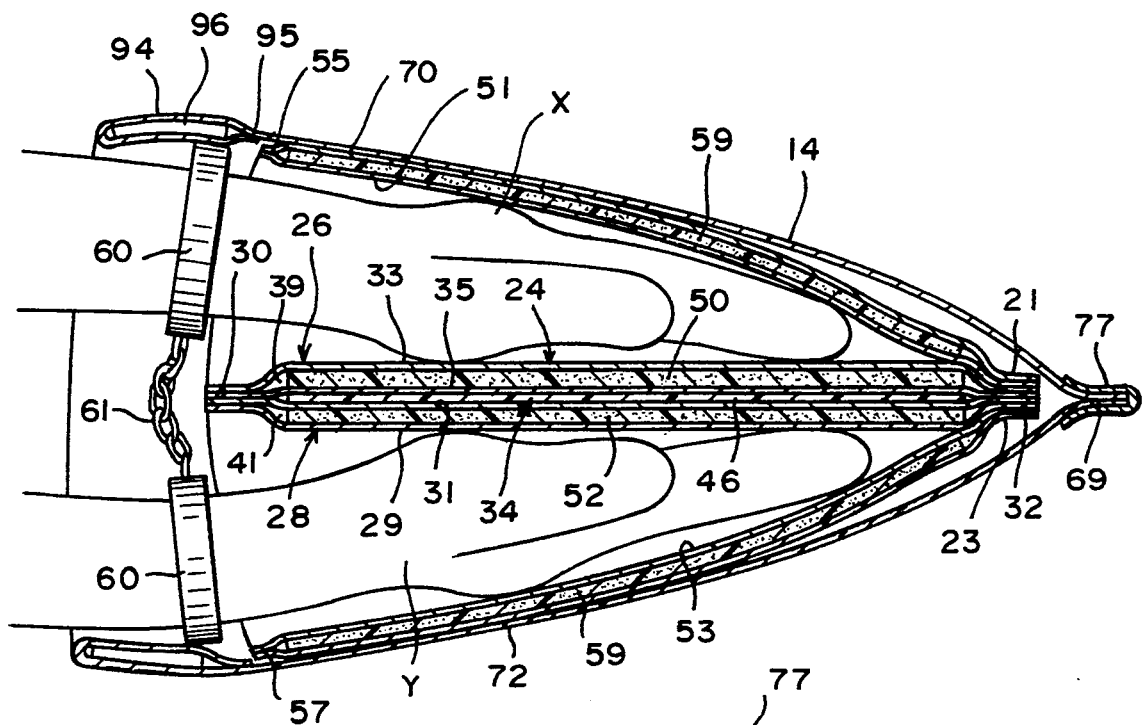
FIG_3
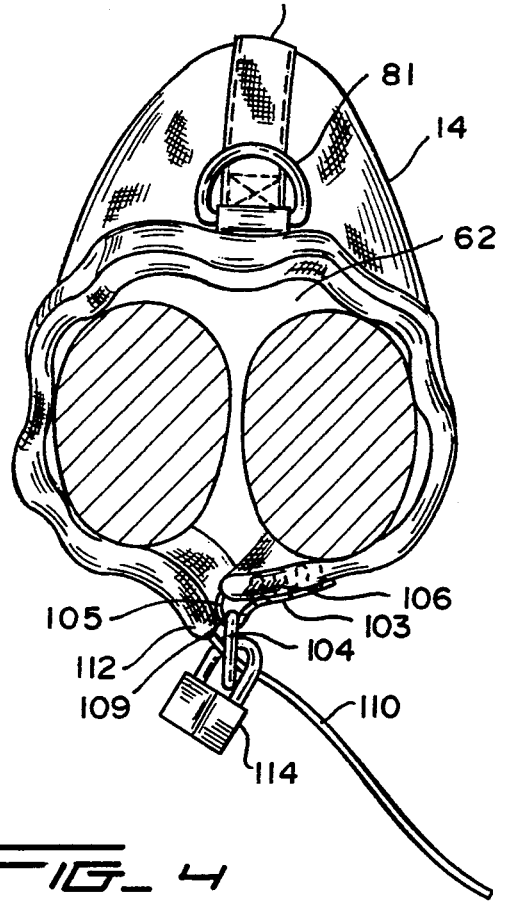
FIG_4

HANDS RESTRAINT FOR HANDCUFFED WRISTS

BACKGROUND OF THE INVENTION

1. Field of the Invention

This invention pertains to restraints for the hands and specifically for hands covering used in connection with handcuffed wrists.

2. Background of the Prior Art

The prior art shows hand coverings designed to restrain movement of the hands.

U.S. Pat. No. 404,544 discloses a pair of mitts connected to handcuffs for use in protecting prisoners in cold weather.

U.S. Pat. No. 3,476,608 shows a hand restraint for a patient in the form of a glove having fastenings to restrain the hand to limit a patient's activity.

U.S. Pat. No. 4,741,051 discloses a protective mitt for use with hand cuffed hands and having a draw string to secure the hand cuffed hands within the mitt.

The above devices are cumbersome to make and are difficult to secure to the hands of the wearer. The present restraint is simple to manufacturer and is easily secured to handcuffed wrists.

SUMMARY OF THE INVENTION

One object of this invention is to provide an inner pouch having an inner central wall panel to separate the hands in palm-to-palm relationship.

It is yet another object o f this invention to provide a hands restraint having an outer pouch covering the inner pouch and having a fastener thereon to secure the inner and outer pouches to the hands and wrists.

Another object of this invention is to provide a lock for the fastener whereby the inner and outer pouches may not be removed without first removing of the lock.

These and other objects of the invention will become apparent to those skilled in the art to which the invention pertains from a reading of the following specification when taken with the annexed drawings.

BRIEF DESCRIPTION OF THE DRAWINGS

FIG. 1 is a perspective view of the hands restraint showing hand cuffed hands inserted in a pouch and a fastener with a lock for securing the pouch on the wrists.

FIG. 2 is an exploded view of the hands restraint showing an inner pouch having plural compartments and having a central wall panel and an outer pouch with a fastener for securing both inner and outer pouch to the wrists.

FIG. 3 is a cutaway cross sectional side view of the hands restraint showing an outer pouch and an inner pouch with a central wall panel separating the hands in palm-to-palm relationship.

FIG. 4 is an end view of the hands restraint showing a fastener for securing the outer pouch to the wrists and a lock to secure the fastener in position.

DETAILED DESCRIPTION OF THE PREFERRED EMBODIMENT OF THE INVENTION

Referring now in more detail to the drawings, FIGS. 1 and 2 show a hands restraint 10 comprising an inner pouch 12 and an outer pouch 14. The inner pouch 12 may be structured from a single piece of material or a double layer of material such as durable fabric folded to form opposed outside walls 16 and 18 and inside walls 20 and 22. The fabric is folded such as to form a central wall 24 comprising a double layer of fabric forming opposed panels 26 and 28, FIG. 3, stitched at the outer edge 30 and inner edge 32. The folded layers of fabric form an open slot 34 between the panels 26 and 28, extending the depth and length of the pouch. The ends 11, 13, and 15 of the folded fabric are stitched along the outer edge 38, FIG. 2, from point 40 to point 42 to form a plural compartments mitt having openings 17 and 19 for insertion of handcuffed hands x and y. A reinforcing plate 46, FIG. 3, occupies the slot 34 and may be removed through the opening 35.

It will be understood that the central panel 24 comprising opposed wall panels 26 and 28 each having outer walls 29 and 31 and inner walls 33 and 35 respectively with spaces 39 and 41 there between and extending between the stitching 30 and 32. The spaces 39 and 41 may be filled with reinforcing material such as foam rubber 50 and 52 or the like. The outer walls 51 and 53 comprising a double layer of material may have reinforcing material 59 similar to 50 and 52. The inner edges 21 and 23 of outer walls 51 and 52 are sewn together with the ends of the inner walls 26 and 28 at 32 to form a closed end as shown.

It will be seen that the wrists of the hands having handcuffs 60 thereon are received into the openings 17 and 19 of pouch 12 such that the central panel 24 separates the hands in palm-to-palm relationship. In this regard, it will be seen that the hands are incapable of grasping objects such as weapons in the case of a prisoner or medical equipment in the case where the pouch is used for restraining a patient's hands.

It is to be noted that the outer stitched edges 55 and 57 of pouch 12 lie below the handcuffs 60. That is, the stitched edges 30, 55, and 57 of pouch 12 do not cover the handcuffs 60, nor are they attached around the wrists. Since the pouch 12 is not secured to the wrists, a second or outer pouch 14 is employed.

FIGS. 2 and 3 show the outer pouch 14 which is larger than the inner pouch 12 and comprises a single piece or double layer of durable water impervious material folded at upper edge 67 and stitched at edge 69 from end 71 to end 73 to form a pouch having opposed outer walls 70 and 72 and an opening 62. A reinforcing tape 77 extending from end 71 to edge 67 is sewn to the edges 67 and 69 and terminates with a ring 81 near edge 67. It will be seen that pouch 14 has a strip of tape 90 of reinforcing material having a ring 92 sewn to the edge 69 as shown.

The pouch 14 has a folded end 94 stitched at 95 to form a slot 96 extending the circumference of the pouch. A strap 98, having metal eyelets 100 is threaded inside the slot 96 and is fastened at one end 103 by stitching 106. It is to be understood that the end 103 of the strap 98 is folded back upon itself and is stitched at 106. Ring 104 is secured in the loop 109. It will be seen that the strap 98 extends about the inside of the slot 96 with the terminal free end 110 exiting at edge 112.

Once the hand cuffed hands are inserted into the inner pouch with the hands separated by the central panel 24, the outer pouch 14 is then pulled over the inner pouch as shown in FIGS. 3 and 4. The leading terminal end 110 of the strap 98 is threaded through the ring 104 and pulled tightly about the wrists to secure the pouch 14 thereto.

A lock 114 threaded through the ring 104 and an selective eyelet 100 secures the leading end 110 of the strap 98 to the ring 104. The lock 114 must be unlocked with a key to remove the pouches 12 and 14.

What I claim is:

1. A restraint for hands wherein the wrists are handcuffed comprising:

an inner pouch including a pair of spaced-apart wall panels;

means joining the panels to one another along the edges thereof forming a bottom at one end and an opening opposite thereto;

an inner wall panel extending substantially equidistantly between said spaced apart wall panels and being secured therein by the means joining said panels to thereby define a pair of compartments whereby a hand is disposed in each through said opening to maintain the fingers of each hand out of contact with the opposite hand; and an outer pouch removably receiving said inner pouch and means on the outer pouch securing each pouch over said handcuffed wrists.

2. A restraint for hands according to claim 1, and said inner wall panel comprises spaced apart panels each having outer walls and inner walls defining spaces having reinforcing means thereon; and an additional space between said spaced apart panels accessible from an outer edge of said central wall.

3. A restraint for hands according to claim 2, and said additional space having reinforcing means removably inserted in said space.

* * * * *